US00PP09568P

United States Patent [19]

Zaiger et al.

[11] Patent Number: Plant 9,568

[45] Date of Patent: Jun. 4, 1996

[54] PLUM TREE MURIETTA

[76] Inventors: Chris F. Zaiger, 929 Grimes Ave.; Gary N. Zaiger, 1907 Elm Ave.; Leith M. Gardner, 1207 Grimes Ave.; Grant G. Zaiger, 4005 California Ave., all of Modesto, Calif. 95358

[21] Appl. No.: 457,132

[22] Filed: Jun. 1, 1995

[51] Int. Cl.[6] ..... A01H 5/00

[52] U.S. Cl. ..... Plt./38.1

[58] Field of Search ..... Plt./38.1, 38.2

*Primary Examiner*—James R. Feyrer

[57] ABSTRACT

The present new and distinct variety of plum tree has the following unique combination of desirable features that are outstanding in a new variety:

1. Fruit with good flavor and eating quality.
2. Fruit with good handling and shipping quality.
3. Heavy and regular production.
4. Vigorous upright growth.
5. Nearly uniform size of fruit throughout the tree.
6. The ability of the fruit to hold firm on the tree 8–10 days after maturity (shipping ripe).

1 Drawing Sheet

ORIGIN OF THE VARIETY

The new and distinct variety of plum tree was originated by us in our experimental orchard as an open pollinated seedling of Friar Plum (non-patented). A large number of these open pollinated seedlings were grown under careful observation by us. One such seedling, the present variety, being especially desirable for its fruit quality and heavy production was selected for asexual reproduction and commercialization.

ASEXUAL REPRODUCTION OF THE VARIETY

The present new variety of plum tree was asexually propagated by budding, as performed by us in our experimental orchard located near Modesto, Calif., which shows that all characteristics of the tree and its fruit run true to form and are established and transmitted through succeeding propagations.

SUMMARY OF THE VARIETY

The new and distinct variety of plum tree is of large size, vigorous, upright in growth and a regularly productive bearer of large, clingstone fruit with good flavor and eating quality. The fruit is further characterized by having firm flesh, holding firm on the tree 8 to 10 days after maturity (shipping ripe), having good storage and shipping quality, and in comparison to its maternal parent Friar Plum (non-patented), the variety is more round in shape and approximately 40 days earlier in maturity.

DESCRIPTION OF THE PHOTOGRAPHS

The accompany color photographs show reproductions of typical specimens of the fruit and foliage of the new variety of plum tree. The upper and lower surface of the leaves are illustrated. The exterior and sectional view show the fruit divided in the suture plane to reveal flesh coloration, pit cavity and a stone remaining in place. The photographs of the fruit were taken shortly after the plums were picked at maturity (firm ripe) and the colors are as nearly true as is reasonably possible in a color representation of this type.

DESCRIPTON OF THE VARIETY

The following is a detailed botanical description of the new variety of plum tree, its flowers, foliage and fruit, as based on observations of specimens grown near Modesto, Calif., with color terminology (except those in common terms) in accordance with Reinhold Color Atlas by a Kornerup and J. H. Wanscher.

Tree:
- *Size.*—Large.
- *Vigor.*—Vigorous.
- *Growth.*—Upright.
- *Density.*—Medium dense.
- *Productivity.*—Productive.
- *Bearing.*—Regular.
- *Form.*—Usually pruned to vase shape.

Trunk:
- *Size.*—Large.
- *Surface.*—Medium shaggy.
- *Color.*—Brown to dark brown (6-E-8) to (7-E-8).

Branches:
- *Size.*—Medium.
- *Surface.*—Smooth to medium rough.
- *Lenticels.*—Numerous. Large size.
- *Color.*—Light brown to brown (6-E-4) to (6-E-5). Varies with age of growth.

Leaves:
- *Size.*—Large. Average length 4¼". Average width 1½".
- *Form.*—Oblanceolate.
- *Texture.*—Smooth.
- *Margin.*—Finely serrated.
- *Petiole.*—Medium size. Medium length. Medium thickness.
- *Glands.*—Globose. Medium size. Number varies from 0 to 3. Average number 2. Positioned on base of leaf blade and upper portion of petiole.
- *Color.*—Upper surface — green to dark green (27-F-4) to (28-F-6). Lower surface — dull green to grayish green (28-E-5) to (28-E-7).

Flower buds:
- *Size.*—Medium.
- *Length.*—Medium.
- *Form.*—Plump-free.

Flowers:
- *Blooming period.*—Date of first bloom Feb. 22, 1994 Date of full bloom Mar. 1, 1994. Varies slightly with climatic conditions.
- *Size.*—Medium.
- *Pollen.*—Present.
- *Color.*—White.

Fruit:

*Maturity when described.*—Firm ripe.

*Date of first picking.*—Jun. 8, 1994.

*Date of last picking.*—Jun. 16, 1994.

*Size.*—Medium to large. Average diameter axially 2⅛". Average transversely in suture plane 2½".

*Form.*—Nearly globose — slightly flattened at stem end.

*Suture.*—Shallow — extends from base to apex.

*Ventral surface.*—Nearly rounded.

*Cavity.*—Rounded to slightly elongated in suture plane. Average depth — ⅜". Average breadth — ½".

*Apex.*—Usualy rounded — varies from rounded to slightly retuse.

*Base.*—Retuse.

*Stem.*—Medium length. Medium width.

Flesh:

*Texture.*—Firm.

*Fibers.*—Very small and tender.

*Ripens.*—Evenly.

*Juice.*—Moderate.

*Flavor.*—Good.

*Eating quality.*—Good.

*Aroma.*—Undetected.

*Color.*—Pale yellow to yellow (4-A-3) to (4-A-5). Pit cavity — yellowish gray to grayish yellow (4-B-3) to (4-B-5).

Skin:

*Thickness.*—Medium.

*Texture.*—Medium to tough — tenacious to flesh.

*Tendency to crack.*—None.

*Bloom.*—Moderate.

*Down.*—Wanting.

*Color.*—Dark magenta to blackish blue (13-F-5) to (19-F-3).

Stone:

*Size.*—Medium. Average length ⅞". Average width ¾". Average thickness ½".

*Type.*—Clingstone.

*Form.*—Oval.

*Sides.*—Mostly equal — slightly larger on suture side

*Surface.*—Slightly pitted throughout — pit cavities vary from round to elongated. Small furrows near the sides.

*Ridges.*—Small ridges on each side of stone near the suture plane.

*Apex.*—Acute.

*Base.*—Usually straight. Varies from round to straight.

*Tendency to split.*—None.

*Color.*—Varies from brown to golden brown (5-C-5) to (5-C-7).

Use: Dessert.

*Market.*—Local and long distance.

Keeping quality: Good.

Shipping quality: Good.

The new and distinct variety of plum tree, its flowers, foliage and fruit herein described may vary in slight detail due to variations in climate, soil conditions and cultural practices under which the variety may be grown. The present description is that of the variety grown under the ecological conditions prevailing near Modesto, Calif.

We claim:

1. A new and distinct variety of plum tree, substantially as illustrated and described, characterized by large size, vigorous upright growth, being a productive and regular bearer of large, firm, yellow flesh, clingstone fruit with good flavor and eating quality and the ability to be shipped to long distance markets, and in comparison to Friar Plum (non-patented) the new variety is approximately 40 days earlier in maturity.

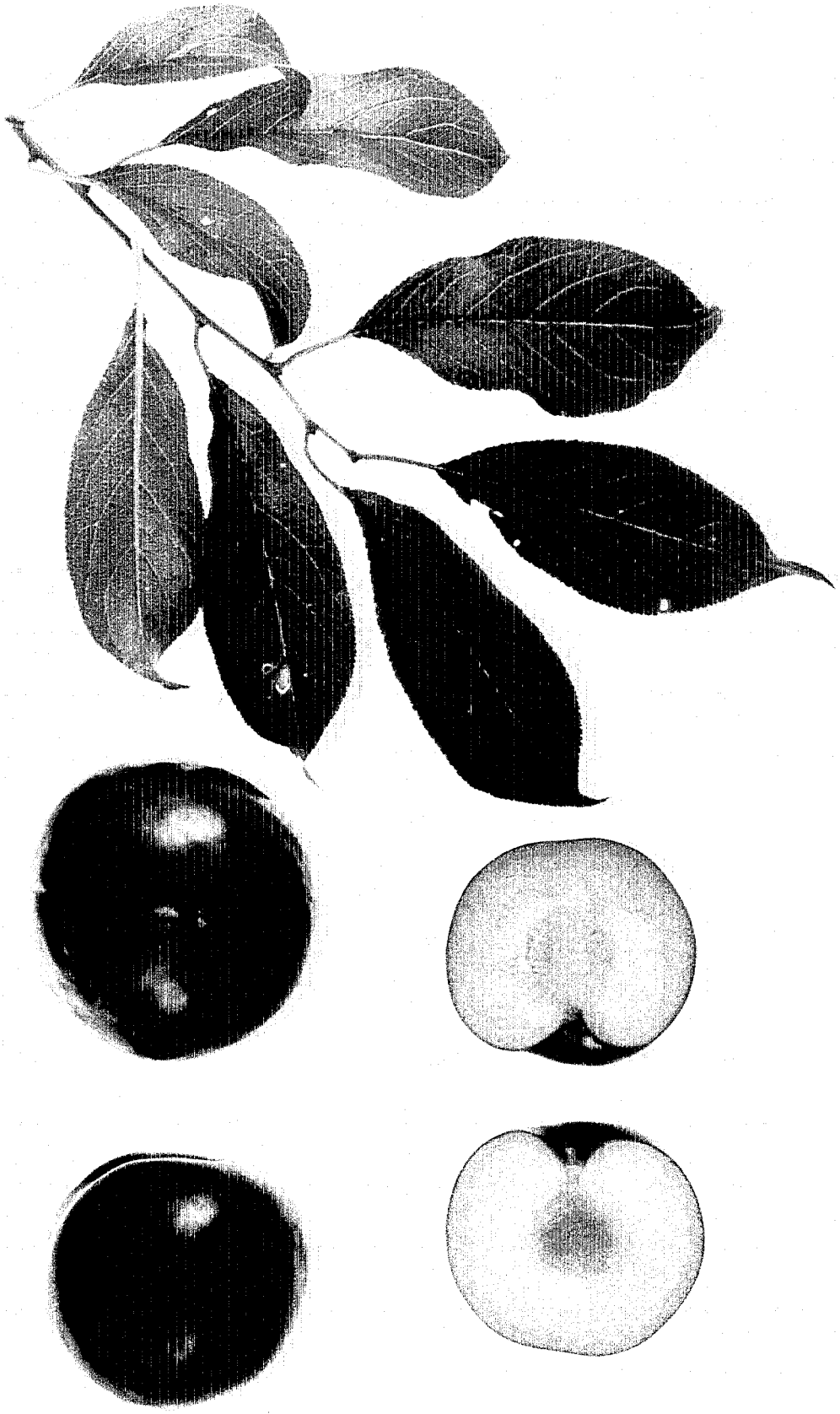

* * * * *